United States Patent [19]
Best et al.

[11] Patent Number: 5,514,797
[45] Date of Patent: May 7, 1996

[54] METHOD FOR INCREASING PURITY OF MELAMINE

[75] Inventors: David Best, Prairieville; Amit Gupta, Baton Rouge, both of La.

[73] Assignee: Melamine Chemicals, Inc., Donaldsonville, La.

[21] Appl. No.: 479,003

[22] Filed: Jun. 7, 1995

[51] Int. Cl.⁶ ............................................. C07D 251/62
[52] U.S. Cl. ................................................. 544/203
[58] Field of Search ................................... 544/203

[56] References Cited

U.S. PATENT DOCUMENTS 4,565,867  1/1986  Thomas et al. ..................... 544/201

*Primary Examiner*—John M. Ford
*Attorney, Agent, or Firm*—Breiner & Breiner

[57] ABSTRACT

A method of purifying melamine produced from urea in a high-pressure, non-catalytic, non-aqueous process is described. In the method impure melamine is heated to a temperature of from about 250° to about 1000° F. under a pressure from about 600 to 3000 psi in the presence of ammonia to provide melamine having a purity of 99.0% or above. The method is economical since chemical treatment and recrystallization steps are not required.

3 Claims, 1 Drawing Sheet

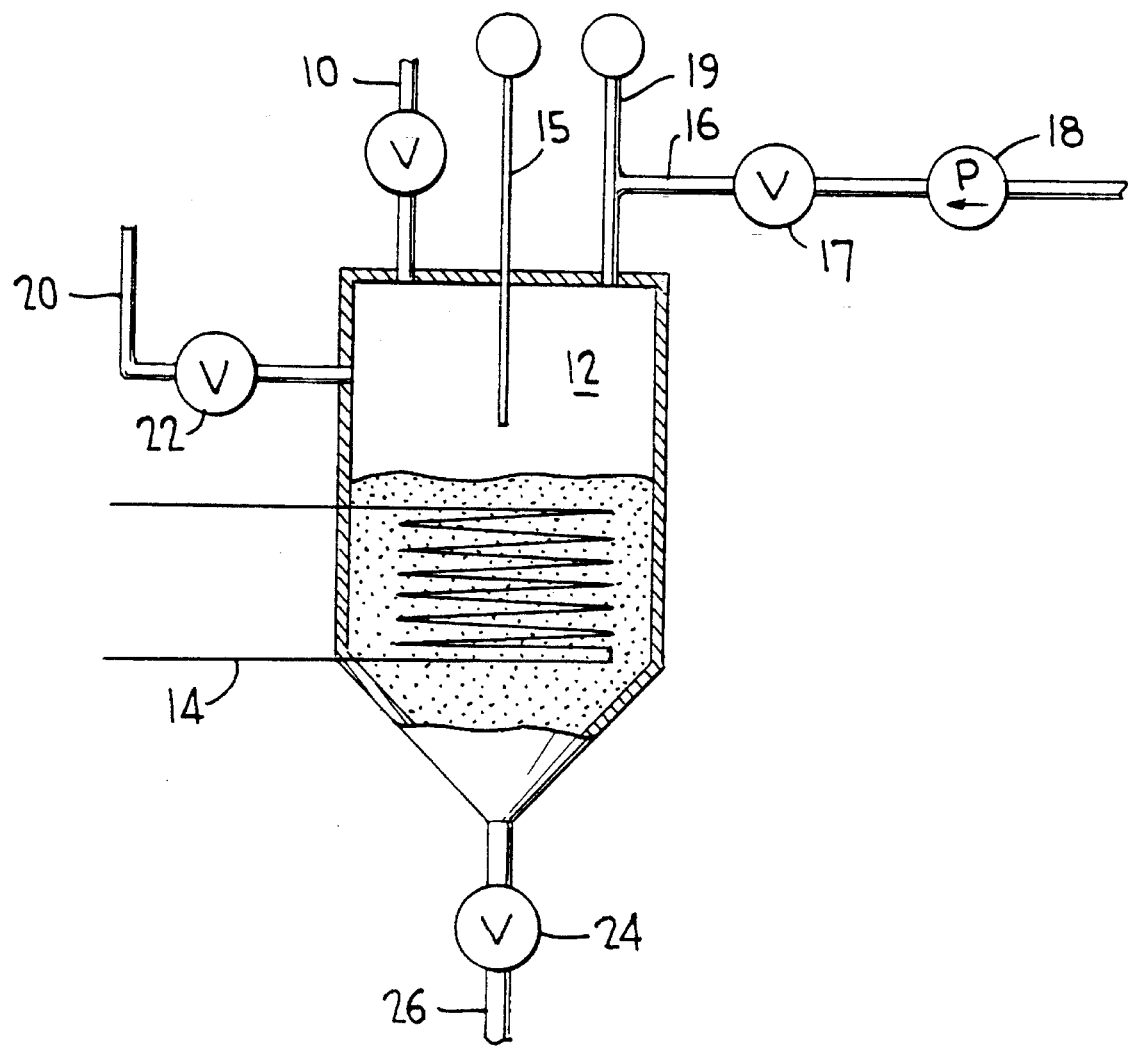

METHOD FOR INCREASING PURITY OF MELAMINE

BACKGROUND OF INVENTION

The present invention is directed to a method for the purification of melamine produced from urea in a high-pressure, non-catalytic, non-aqueous process. More particularly, the present invention is directed to a process wherein melamine is heated to a temperature of from about 250° to about 1000° F. under pressure of from about 600 to about 3000 psi in the presence of ammonia to provide melamine having a purity of 99.0% or above.

Background of Invention

Melamine is commercially produced by heating urea to provide melamine and ammonia and carbon dioxide as by products. The basic reaction is

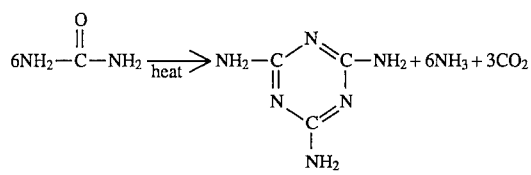

The commercial processes of providing melamine from urea are either high-pressure, non-catalytic or low-pressure and catalytic using a catalyst such as alumina. Conventionally, in low-pressure, catalytic processes the melamine is recovered in an impure form and, subsequently, recrystallized using a chemical treatment to provide melamine which is essentially 100% pure. Similar, chemical treatment and recrystallization steps were used in producing pure melamine from the melamine produced in a high-pressure, non-catalytic process.

U.S. Pat. No. 4,565,867 issued Jan. 21, 1986 and assigned to the assignee of the present application, describes a high-pressure process wherein the melamine is recovered at a relatively high purity and used in that form without chemical treatment or a recrystallization step. The process is highly efficient and provides a low cost melamine. The melamine produced by the '867 patent process, as stated in the patent, has a purity in the range of 96 to 99.5% melamine which contains low levels of melem and melam impurities. However, the process of the '867 patent in commercial operation has only produced melamine in the range of about 97.5% with the main impurities being melem, melam, uredi-omelamine and ammeline. Although this product is usable in most melamine markets, it is limited in some because of the impurities.

Accordingly, there is a need for a method for producing a more pure melamine, namely 99+ percent, on a commercial basis without either recrystallizing or having to dispose of by-products of the purification.

OBJECTS AND SUMMARY OF THE INVENTION

It is a primary object of the present invention to provide a method for increasing the purity of melamine produced by an anhydrous high-pressure melamine synthesis process without the need to dispose of the impurities or to require an expensive recrystallization step.

The aforesaid and other objectives of this invention are accomplished by heating melamine to a temperature of from about 250° F. to about 1000° F., preferably from about 500° F. to 800° F. under pressure of about 600 to about 3000 psi, preferably from about 1200 to 1400 psi, at the solidification point of melamine in the presence of ammonia. Without intending to be limiting, it is theorized that in the production of melamine low amounts of melam and melem are formed. It is believed that heating the low purity melamine in the presence of ammonia and at increased temperatures and pressures results in a reversal of the reaction leading to the formation of the melam and melem, according to the following equation:

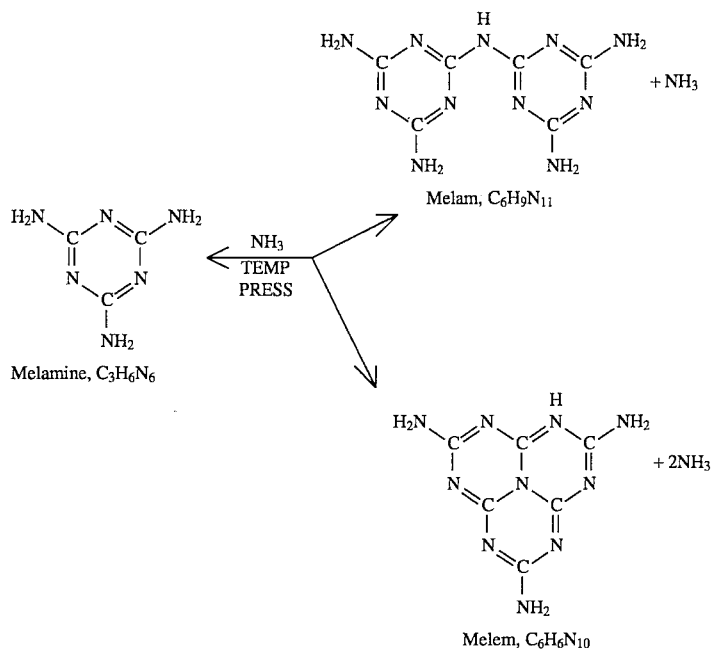

This theory is supported in that, as will be described in the examples hereinafter, when treating the impure melamine with ammonia in accordance with the present invention, there is an increase in weight of the starting product which is consistent with the analytically determined amount of melam and melem which is found in the impure product.

Accordingly, not only are the impurities eliminated without need for recrystallization or chemical treatment or a need to dispose of the impurities, the present invention provides an increased benefit due to the amount of melamine product produced.

THE DRAWING AND DETAILED DESCRIPTION

Having described the invention in general terms a detailed description of preferred embodiments will be described in relation to the drawing. The single FIGURE of the drawing sets forth in diagramical form a reactor for carrying out the process of the present invention.

Referring to the drawing, melamine powder is charged through line 10 into vessel 12. The vessel is heated to a temperature in the range of about 250° to 1000° F., and preferably from about 500° to 800° F. using heating elements 14. At the designated temperature the pressure in the vessel 12 is increased to the desired range, i.e., from about 600 to 3000 psi and preferably at about 1200 to 1600 psi, by injecting ammonia into the vessel through valve 17 and line 16 with pump 18. The temperature and pressure is measured by temperature probe 15 and pressure sensor 19. The heating is then continued to the desired range. The pressure is controlled by releasing ammonia through valve 22 and line 20 as necessary. The reactor and melamine are then rapidly cooled. The pressure is lowered to atmospheric by bleeding the remaining ammonia through valve 22 and line 20. Dump valve 24 is opened to empty vessel 12 through line 26.

Using the reactor and procedure described above, impure melamine was purified according to the following examples.

EXAMPLE 1

100 parts of melamine having a purity of 97.5% was heated to 400° F. in an insulated reactor 12 without pressure. Thereafter, ammonia was added through line 16 by opening valve 17 thereby pressurizing the reactor to 1000 psi. Heating was then continued to a temperature of 750° F. while adjusting the pressure in the vessel by releasing vaporous ammonia by adjusting valve 22. The reactor was held at 750° F. for 30 minutes. Thereafter, the reactor was cooled rapidly by discontinuing heat and removing insulation from the reactor. Although it is possible to cool using liquid ammonia or other means, this is not essential.

The impure melamine employed was designated M-II. The weight before starting and at the end of the treatment was determined as follows:

| M-II | gross | 45.8414 | |
|---|---|---|---|
| | Tare | 24.3244 | |
| | Net | 21.5170 | |
| | starting | 20.9723 | |
| Net gain | | 0.5447 grams | 2.5972% |

The M-II product had impurities at the start of the reaction and at the end of two separate runs, as follows:

| Analysis | M-II Start | Final | |
|---|---|---|---|
| Ammelide | 0 | 0 | 0 |
| Ammeline | 0.1442 | 0.015 | 0.439 |
| Melamine | 97.5 | 99.62 | 99.8 |
| Uredio | 0.0657 | 0 | 0 |
| Melem | 0.139 | 0.3644 | 0.1460 |
| Melam | 1.9215 | 0.0 | 0.0 |

The weight gain in the M-II sample is consistent with the conversion of the melem and melam to melamine.

EXAMPLE 2

100 parts of melamine having a purity of 97.5% was heated to 400° F. in an insulated reactor 12 without pressure. Thereafter, ammonia was added through line 16 by opening valve 17 thereby pressurizing the reactor to 800 psi. Heating was then continued to a temperature of 750° F. while adjusting the pressure in the vessel by releasing vaporous ammonia by adjusting valve 22. The reactor was held at 750° F. for 30 minutes. Thereafter, the reactor was cooled rapidly by discontinuing heat and removing insulation from the reactor. The impure melamine, designated M-II, had impurities at the start of the reaction and at the end of three separate runs, as follows:

| Analysis | M-II Start | Final | | |
|---|---|---|---|---|
| Ammelide | 0 | 0 | 0 | 0.0035 |
| Ammeline | 0.1142 | 0.0387 | 0.0876 | 0.0575 |
| Melamine | 97.5 | 99.04 | 98.87 | 98.80 |
| Uredio | 0.0657 | 0 | 0 | 0 |
| Melem | 0.139 | 0.4904 | 0.5191 | 0.7415 |
| Melam | 1.9215 | 0.0 | 0.0202 | 0.0070 |

EXAMPLE 3

100 parts of melamine having a purity of 97.5% was heated to 400° F. in an insulated reactor 12 without pressure. Thereafter, ammonia was added through line 16 by opening valve 17 thereby pressurizing the reactor to 1200 psi. Heating was then continued to a temperature of 750° F. while adjusting the pressure in the vessel by releasing vaporous ammonia by adjusting valve 22. The reactor was held at 750° F. for 30 minutes. Thereafter, the reactor was cooled rapidly by discontinuing heat and removing insulation from the reactor.

The impure melamine employed was designated M-II. The M-II product had impurities at the start of the reaction and at the end of three separate runs, as follows:

| Analysis | M-II Start | Final | | |
|---|---|---|---|---|
| Ammelide | 0 | 0.0096 | 0.0101 | 0.004 |
| Ammeline | 0.1142 | 0.0985 | 0.0657 | 0.578 |
| Melamine | 97.5 | 99.75 | 99.82 | 99.86 |
| Uredio | 0.0657 | 0.0 | 0 | 0 |
| Melem | 0.139 | 0.138 | 0.098 | 0.0765 |
| Melam | 1.9215 | 0 | 0 | 0 |

The present invention, as is apparent, provides a method of increasing the purity of melamine without need for chemical treatment and without need for a recrystallization process.

As will be apparent to one skilled in the art, various modification can be made within the scope of the above description. For example, the invention is described in reference to impure melamine produced according to a high pressure, non-catalytic process. However, it can be applied to melamine produced by a low pressure, catalytic process provided the catalyst is separated from the melamine. Such modification being within the ability of one skilled in the art form a part of the present invention and are embraced by the appended claims.

It is claimed:

1. A method for purifying melamine comprising the steps of feeding impure melamine into a reactor; heating the melamine in the reactor to a temperature between about 250° to about 1000° F. under pressure of from about 600 to about 3000 psi while adding ammonia to said reactor and recovering melamine in purified form.

2. The method of claim 1 wherein the impure melamine is produced from urea in a high-pressure, non-catalytic, non-aqueous process.

3. The process of claims 1 or 2 wherein the melamine is heated between about 500° and 800° F. under a pressure of about 800 to 1400 psi.

* * * * *